United States Patent [19]

Higuchi et al.

[11] Patent Number: 5,087,737

[45] Date of Patent: * Feb. 11, 1992

[54] PROCESS FOR PRODUCING METHYL METHACRYLATE

[75] Inventors: Hirofumi Higuchi; Koichi Kida; Shuji Ebata, all of Niigata, Japan

[73] Assignee: Mitsubishi Gas Chemical Company, Inc., Tokyo, Japan

[*] Notice: The portion of the term of this patent subsequent to Feb. 11, 2009 has been disclaimed.

[21] Appl. No.: 529,910

[22] Filed: May 29, 1990

[30] Foreign Application Priority Data

Jul. 4, 1989 [JP] Japan .................... 1-171190

[51] Int. Cl.⁵ ............................... C07C 67/20
[52] U.S. Cl. ..................... 560/215; 560/211
[58] Field of Search ............................ 560/215

[56] References Cited

FOREIGN PATENT DOCUMENTS

DE3436608  5/1985  European Pat. Off. .
2528524   11/1976  Fed. Rep. of Germany .
58-183654 10/1983  Japan .
60-78937   5/1985  Japan .
58-55444   4/1988  Japan .

OTHER PUBLICATIONS

Patent Abstracts of Japan; vol. 14, No. 68(C-686)(4011), Feb. 8, 1990, JP-A-1290653, Nov. 22, 1989.

*Primary Examiner*—Paul J. Killos
*Attorney, Agent, or Firm*—Frishauf, Holtz, Goodman & Woodward

[57] ABSTRACT

Disclosed is a process for producing methyl methacrylate which comprises:

(I) a step of reacting prussic acid and acetone to form acetonecyanhydrin;

(II) a step of hydrating the acetonecyanhydrin obtained in the step (I) to form α-hydroxyisobutyric acid amide;

(III) a step of dehydrating the α-hydroxyisobutyric acid amide obtained in the step (II) to form methacrylic acid amide;

(IV) a step of reacting the methacrylic acid amide obtained in the step (III) and methyl formate to form methyl methacrylate and formamide; and (V) a step of dehydrating formamide separated from the product obtained in the step (IV) to form prussic acid and recycling said prussic acid as a starting material in the step (I).

The process produces methyl methacrylate with high selectivity without undesirable by-product such as ammonium sulfate.

13 Claims, No Drawings

PROCESS FOR PRODUCING METHYL METHACRYLATE

BACKGROUND OF THE INVENTION

1. Field of the Invention

The present invention relates to a novel process for producing methyl methacrylate from acetone and methyl formate, or from acetone, methanol and carbon monoxide as starting materials.

A large amount of methyl methacrylate is used as a starting material for production of various polymers and the methyl methacrylate is a greatly important intermediate in industrial use.

2. Description of Related Arts

For production of methyl methacrylate on a commercial scale, an acetone cyanhydrin method in which prussic acid and acetone are used as starting materials, and methyl methacrylate is produced through acetone cyanhydrin (hereinafter referred to as "ACH") formed from the starting materials, and a $C_4$ oxidation method in which isobutylene or tert-butanol is used as a starting material have been put into practical use.

In addition, it has been proposed that methyl methacrylate can be produced by an oxidation-dehydrogenation of isobutyric acid, or a condensation-dehydration of propionic acid or propion aldehyde and formaldehyde. But, these methods have not been put into practice.

In accordance with the ACH method, ACH is synthesized from prussic acid and acetone, and then the resulting ACH is reacted with methanol in the presence of an excess amount of concentrated sulfuric acid to produce methyl methacrylate. This ACH method is widely carried out now, because the reaction proceeds easily with high yields. The ACH method, however, has disadvantages in that large amounts of waste sulfuric acid and ammonium sulfate are by-produced and the treatment thereof increases production costs of methyl methacrylate.

Also the $C_4$ method has disadvantages in that a number of side reactions are caused, the yield of methyl methacrylate is low, purification costs are high, the operations are complicated, and an expensive reactor is required. In addition, isobutylene and tert-butanol to be used as starting materials are not easily available.

SUMMARY OF THE INVENTION

An object of the present invention is to provide a novel process for production of methyl methacrylate from starting materials easily available and in stable supply.

Another object of the present invention is to provide a process for production of methyl methacrylate with simple operations at low cost.

Still another object of the present invention is to provide a process for production of methyl methacrylate in which starting materials can circulate by regeneration during reactions.

The present invention relates to a process for producing methyl methacrylate which comprises:

(I) a step of reacting prussic acid and acetone to form acetone cyanhydrin (ACH);

(II) a step of hydrating ACH obtained in the above step (I) to form α-hydroxyisobutyric acid amide;

(III) a step of dehydrating α-hydroxyisobutyric acid amide obtained in the above step (II) to form methacrylic acid amide;

(IV) a step of reacting methacrylic acid amide obtained in the above step (III) with methyl formate or with methanol and carbon monoxide to form methyl methacrylate and formamide; and (V) a step of dehydrating formamide separated from the product obtained in the above step (IV) to form prussic acid and recycling the prussic acid as a regenerated starting material in the step (I).

DESCRIPTION OF PREFERRED EMBODIMENTS

The process of the present invention eventually employs acetone and methyl formate, or acetone, methanol and carbon monoxid as starting materials. Although the process of the present invention produces the objective methyl methacrylate through ACH, it is not accompanied by by-production of ammonium sulfate at all unlike the conventional ACH method.

Acetone is formed as a by-product in large amounts and at low cost in production of phenol by a cumene method. If necessary, it can easily be produced from propylene.

Methyl formate can easily be produced through carbonylation or dehydrogenation of methanol which is commercially available in large amounts and at low cost.

In the process of the present invention, ACH is produced by reacting prussic acid and acetone by the conventional methods. More specifically, ACH can be produced in a high yield by reacting prussic acid and acetone at a temperature as low as about 10° C. in the presence of a basic catalyst such as alkalis or amines.

α-Hydroxyisobutyric acid amide is produced by reacting ACH and water in the presence of a catalyst. As such catalysts, those effective for the hydration reaction of nitriles can be used. Although strong acids such as sulfuric acid can be used, metal or metal oxide catalysts are desirable from an economical standpoint including post-treatment. More specifically, manganese, copper, nickel and their oxides are effective, with manganese oxide being particularly preferred.

The weight ratio of ACH to water is suitable to be in a range of 10:90 to 90:10. In the reaction system, a solvent such as acetone or methanol can be also present. When manganese oxide is used as a catalyst, the reaction temperature is preferably 20° to 150° C. and more preferably 40° to 100° C. The reaction time is preferably 0.3 to 6 hours and more preferably 0.5 to 3 hours. The reaction can be carried out batchwise or continuously.

Although production of methacrylic acid amide by a dehydration reaction of α-hydroxyisobutyric acid amide can be carried out by a liquid phase reaction using, for example, sulfuric acid or phosphoric acid, it can be carried out more effectively by a gas phase reaction using a solid catalyst.

In connection with catalysts for the gas phase catalytic reaction, Japanese Patent Application Laid-Open No. 183654/1983 discloses a process in which a solid acid catalyst such as solid phosphate is used. This process, however, has a disadvantage in that a large amount of methacrylic acid is by-produced. In the process of the present invention, normally the nitrogen atoms are recycled between amide and nitrile in the reaction system, but undesirable by-production of methacrylic acid leads to taking nitrogen atoms out of the reaction cycle whereby it becomes difficult to make the process advantageous from an economical standpoint.

According to the present invention, use of an amide compound as a diluent in the dehydration reaction prevents methacrylic acid as a by-product from forming and permits production of the objective product with high selectivity at a high conversion of the starting materials.

Amide compounds which can be used include dimethyl formamide, dimethylacetamide, and N-methylpyrrolidone. Of these compounds, N-methylpyrrolidone is particularly preferred.

In the process of the present invention, the reaction of methacrylic acid amide and methyl formate, or the reaction of methacrylic acid amide, methanol and carbon monoxide for production of methyl methacrylate can be effectively carried out in the presence of a solvent and a catalyst, although it proceeds only by heating a mixture of methacrylic acid amide and methyl formate in the absence of a catalyst.

Since the above reaction is an equilibrium reaction, the yield of methyl methacrylate varies with the molar ratio of methacrylic acid amide to methyl formate, or to methanol and carbon monoxide. The molar ratio of methacrylic acid amide to methyl formate, or to methanol and carbon moxide is preferably 1:1 to 10:1 and more preferably 2:1 to 5:1.

Addition of a solvent is effective in increasing the solubility of solid methacrylic acid amide, and the selectivity of the reaction. As the solvent to be used, methanol is most preferable, and the molar ratio of methanol to methacrylic acid amide is preferably 2:1 to 10:1.

Known catalysts to be used in the above reaction include inorganic acids, organic acids, alkalis, and their salts as described in Japanese Patent Application Laid-Open Nos. 55444/1983 and 78937/1985. However, when these known catalysts are used, both the rate of reaction and selectivity are insufficiently low.

Alkali metal alcolate and alakaline earth metal oxide are excellent as catalysts for use in the above reaction.

Representative examples of the alkali metal alcolate to be used as a catalyst in the process of the present invention are methylate, ethylate and butyrate of sodium and potassium. They can be prepared from metallic lithium, sodium or potassium and lower alcohol.

The alkaline earth metal oxide to be used as a catalyst in the process of the present invention includes magnesium oxide, calcium oxide, and barium oxide.

In connection with reaction conditions, when the alkali metal alcolate or alkaline earth metal oxide is used as a catalyst in the process of the present invention, the suitable amount of the catalyst used is 0.001 to 0.30 per mol of methacrylic acid amide under conditions that the reaction temperature is 20° to 100° C. and the reaction time is 0.5 to 6 hours.

Japanese Patent Application Laid-Open No. 3015/1977 discloses that an alkali metal alcolate catalyst is used in production of carboxylic acid ester from carboxylic acid amide and alcohol.

This alcoholysis, however, has a disadvantage in that the yield of carboxylic acid ester is low, as well as operational disadvantages in that the reaction temperature must be as high as 200° C., high pressure is needed and the intermittent release of the pressure in the reaction system is required since ammonia is generated during the reaction.

On the contrary, in the process of the present invention, when an esterification reaction by using methyl formate is carried out, the aforementioned disadvantages can be all dissolved.

In the process of the present invention, the reaction product is separated and recovered by an operation such as distillation, and unreacted materials can be used again as starting materials.

Formamide by-produced along with the objective methyl methacrylate is subjected to a dehydration reaction to produce prussic acid. This prussic acid is separated and recovered, and then reintroduced to the reactor for production of ACH.

In the process of the present invention, the reaction proceeds with high selectivity at each step, and thus methyl methacrylate can be produced with high selectivity from acetone and methyl formate, or from acetone, methanol and carbon monoxide. Moreover, undesirable by-products, such as ammonium sulfate produced in the conventional methods, are not formed at all, and thus the process of the present invention is of high industrial value.

The present invention is described in greater detail with reference to the following examples, although it is not limited thereto.

EXAMPLE 1

Step (I)

Synthesis of ACH from prussic acid and acetone 116 g of acetone and 1 ml of a 1N aqueous sodium hydroxide solution were placed in a 500-milliliter flask equipped with a stirrer, a thermometer, and a dropping funnel for prussic acid, and 59.4 g of prussic acid was dropped thereto while maintaining the temperature in the flask at 20° C. After dropping of prussic acid was completed, the reaction was completed by maintaining the mixture at 20° C. for 2 hours. Then 50% sulfuric acid was added thereto to adjust the reaction solution to pH 3.

The flask was connected to a vacuum system, and unreacted prussic acid was distilled away to obtain 171 g of ACH.

The purity of ACH was 98.4%, and the yield of ACH based on acetone was 99%.

Step (II)

Synthesis of α-hydroxyisobutyric acid amide by hydration of ACH 63.2 g of potassium permanganate and 500 g of water were placed in a 1-liter flask equipped with a stirrer, a reflux cooler and a thermometer, and stirred while heating at 70° C. Then, 240 g of an aqueous solution containing 96.2 g of manganese sulfate and 40 g of 15% sulfuric acid were added thereto, and reacted at 70° C. for 3 hours.

The contents in the flask were cooled, and then a resulting precipitate was suction filtered and washed with 2.4 L (L=liter) of water. The precipitated cake was dried at 60° C. overnight to obtain 74 g of active manganese dioxide, which was used as a catalyst in the subsequent step.

150 g of ACH obtained in the step (I), 350 g of water, 100 g of acetone, and 60 g of manganese dioxide were placed in a 1-liter flask equipped with a stirrer, a reflux cooler and a thermometer, and reacted by heating at 60° C. for 5 hours while stirring.

The reaction solution was cooled with ice, and then the catalyst was removed by suction filtration. A gas chromatographic analysis of the filtrate showed that the conversion of ACH was 99.5%, the yield of α-hydroxyisobutyric acid amide was 95%, and small amounts of acetone and formamide were contained.

The above filtrate was distilled under reduced pressure to obtain 155 g of α-hydroxyisobutyric acid amide with a purity of not less than 99.5% as a main component.

Step (III)

Synthesis of methacrylic acid amide by dehydration of α-hydroxyisobutyric acid amide 20.3 g of sodium hydroxide was dissolved in 100 ml of water, and 10.1 g of magnesium oxide was suspended therein. To this suspension, 116.4 g of 85% phosphoric acid was gradually poured and mixed. Then, the resulting mixture was heated while stirring to evaporate water, thereby making it paste-like, and this paste was calcined at 700° C. for 12 hours. This calcined material was ground to 10-16 mesh, and a 20 ml portion thereof was packed in a tubular reactor made of Pyrex glass with an inner diameter of 18 mm. On the calcained material as packed above, 10 ml of a porcelain Raschig ring with a diameter of 3 mm was placed to form an evaporation zone. While maintaining the reactor at 320° C. and flowing nitrogen gas from the top of the reactor at a rate of 10 ml/min, a 30 wt% N-methylpyrrolidone solution of α-hydroxyisobutyric acid amide obtained in the step (II) was supplied at a rate of 10.5 g/hr.

Reaction gas was collected by cooling with ice and analyzed by a gas chromatography.

The conversion of the α-hydroxyisobutyric acid amide as starting material was 95.8%, and the yield of methacrylic acid amide based on the converted starting material was 81.6 mol %. In addition, 10% of acetone and 4% of acetonitrile were formed, and no methacrylic acid was detected.

600 g of the reaction solution was distilled under reduced pressure to obtain 113 g of methacrylamide with a purity of not less than 98% as a main component.

Step (IV)

Synthesis of methyl methacrylate and formamide from methacrylic acid amide and methyl formate 85.6 g of methacrylic acid amide obtained in the step (III), 180 g of methyl formate, 96 g of methanol, and 1.1 g of sodium methylate were placed in a 1-liter stainless steel autoclave equipped with a stirrer, and reacted by heating at 60° C. for 2 hours while stirring.

The reaction product was cooled, and analyzed by gas chromatography. This analysis showed that the conversion of methacrylic acid amide was 94%, the selectivity of methyl methacrylate based on methacrylic acid amide was 91%, and the selectivity of formamide was 98%. In addition, 8% of methyl α-methoxyisobutyrate was obtained in a yield of 8%.

After neutralization of sodium methylate in the reaction solution with hydrochloric acid, distillation was conducted by the usual method to recover methyl formate, methanol and methacrylic acid amide, and at the same time, 79 g of methyl methacrylate with a purity of 99% and 40 g of formamide with a purity of 99% were obtained.

Step (V)

Production of prussic acid by dehydration of formamide 30 ml of a spherical α-alumina catalyst (calcined at 1,500° C. for 2 hours) with a diameter of 2 mm was packed in a SUS 316 reactor with an inner diameter of 18 mm, and a small amount of dilution nitrogen gas and formamide obtained in the step (IV) were continuously supplied under conditions that the pressure was 80 Torr, the temperature was 450° to 500° C, and the contact time was 0.1 second. The reaction was continued for 10 hours. Non-condensed gas was introduced into a gas washing container containing water to make prussic acid accompanied absorbed therein.

The condensed solution and the absorbing solution were analyzed. This analysis showed that the conversion of formamide was 98%, and the yield of prussic acid based on formamide was 92%.

Upon distillation of the product, high purity prussic acid was obtained. This prussic acid was recycled as a starting material for production of ACH.

COMPARATIVE EXAMPLE 1

At the step (III) of Example 1, the reaction was carried out in the same manner as in Example 1 except that an aqueous solution was used in place of the N-methylpyrrolidone solution. As a result, the conversion of the α-hydroxyisobutyric acid amide as starting material was 98.6%, and the yield of methacrylic acid amide based on the converted starting material was 41.8 ol %. In addition, 32% of methacrylic acid, 10% of acetone, and 8% of methacrylonitrile were formed.

EXAMPLE 2

At the step (IV) of Example 1, 200 g of methanol was supplied in place of 180 g of methyl formate and 96 g of methanol, and carbon monoxide was introduced under a pressure of 40 atm. The reaction was carried out by heating while stirring.

When the temperature in the autoclave reached 60° C., carbon monoxide was introduced so as to maintain the reaction pressure at 40 atm, and the reaction was further continued for 3 hours.

Then, the temperature in the autoclave was lowered to 10° C. by cooling, and the pressure was gradually decreased to atmospheric pressure. Thereafter the reaction product was taken out and analyzed by gas chromatography. This analysis showed that the conversion of methacrylic acid amide was 87%.

The selectivity of methyl methacrylate, and the selectivity of formamide both based on methacrylic acid amide were 95% and 94%, respectively.

What is claimed is:

1. A process for producing methyl methacrylate which comprises:

(I) a step of reacting prussic acid and acetone to form acetonecyanhydrin;

(II) a step of hydrating the acetonecyanhydrin obtained in the step (I) to form α-hydroxyisobutyric acid amide;

(III) a step of dehydrating the α-hydroxyisobutyric acid amide obtained in the step (II) to form methacrylic acid amide;

(IV) a step of reacting the methacrylic acid amide obtained in the step (III) and methyl formate to form methyl methacrylate and formamide; and (V) a step of dehydrating formamide separated from the product obtained in the step (IV) to form prussic acid and recycling said prussic acid as a starting material in the step (I).

2. A process for producing methyl methacrylate which comprises:

(I) a step of reacting prussic acid and acetone to form acetonecyanhydrin;

(II) a step of hydrating the acetonecyanhydrin obtained in the step (I) to form α-hydroxyisobutyric acid amide;

(III) a step of dehydrating the α-hydroxyisobutyric acid amide obtained in the step (II) to form methacrylic acid amide;

(IV) a step of reacting the methacrylic acid amide obtained in the step (III) with methanol and carbon monoxide to form methyl methacrylate and formamide; and (V) a step of dehydrating formamide separated from the product obtained in the step (IV) to form prussic acid and recycling said prussic acid as a starting material in the step (I).

3. The process as claimed in claim 1 or 2, wherein the reaction of prussic acid and acetone in the step (I) is carried out in the presence of a basic catalyst.

4. The process as claimed in claim 1 or 2, wherein the hydration of acetonecyanhydrin in the step (II) is carried out in the presence of a catalyst selected from manganese, copper, nickel or oxide thereof.

5. The process as claimed in claim 1 or 2, wherein the dehydration of α-hydroxyisobutyric acid amide in the step (III) is carried out in a gas phase using an amide compound as a diluting agent.

6. The process as claimed in claim 5, wherein the amide compound is N-methylpyrrolidone.

7. The process as claimed in claim 1, wherein the reaction of methacrylic acid amide and methyl formate in the step (IV) is carried out in a solvent and in the presence of a catalyst.

8. The process as claimed in claim 2, wherein the reaction of methacrylic acid amide with methanol and carbon monoxide is carried out in a solvent and in the presence of a catalyst.

9. The process as claimed in claim 1, wherein the molar ratio of methacrylic acid amide to methyl formate is 1:1 to 10:1.

10. The process as claimed in claim 2, wherein the molar ratio of methacrylic acid amide to methanol or carbon monoxide is 1:1 to 10:1.

11. The process as claimed in claim 7, wherein the catalyst is alkali metal alcolate or alkaline earth metal oxide.

12. The process as claimed in claim 11, wherein the alkali metal alcolate is sodium methylate, sodium ethylate, sodium butyrate, potassium methylate, potassium ethylate, or potassium butyrate.

13. The process as claimed in claim 11, wherein the alkaline earth metal oxide is magnesium oxide, calcium oxide, or barium oxide.

* * * * *

UNITED STATES PATENT AND TRADEMARK OFFICE
CERTIFICATE OF CORRECTION

PATENT NO. : 5,087,737

DATED : February 11, 1992

INVENTOR(S) : HIGUCHI et al

It is certified that error appears in the above-identified patent and that said Letters Patent is hereby corrected as shown below:

Title page, under "[56] References Cited", insert

---U.S. PATENT DOCUMENTS 4,613,685    9/1986    Aoyama et al--

Signed and Sealed this

First Day of November, 1994

*Attest:*

BRUCE LEHMAN

*Attesting Officer*    *Commissioner of Patents and Trademarks*